(12) United States Patent
Hayashi

(10) Patent No.: US 6,168,437 B1
(45) Date of Patent: Jan. 2, 2001

(54) SEAL FOR HARD TISSUE, PRODUCING APPARATUS THEREFOR, AND METHOD FOR ATTACHING SEAL ON HARD TISSUE

(76) Inventor: Shunsuke Hayashi, 5-7, Suehiro 2 Jyo 11-chome, Asahikawa-shi, Hokkaido (JP)

(*) Notice: Under 35 U.S.C. 154(b), the term of this patent shall be extended for 0 days.

(21) Appl. No.: 09/055,737

(22) Filed: Apr. 6, 1998

(30) Foreign Application Priority Data

Apr. 16, 1997 (JP) ................................ 9-114297
Oct. 4, 1997 (JP) ................................ 9-287655
Dec. 21, 1997 (JP) ................................ 9-364995

(51) Int. Cl.⁷ ................................ A61C 5/00
(52) U.S. Cl. ................................ 433/215; 433/222.1
(58) Field of Search ................................ 433/215, 217.1, 433/222.1, 218

(56) References Cited

U.S. PATENT DOCUMENTS 4,795,601 * 1/1989 Cheng ................................ 264/138
5,348,475 * 9/1994 Waknine et al. ................................ 433/215

* cited by examiner

Primary Examiner—John J. Wilson
(74) Attorney, Agent, or Firm—Reed Smith LLP

(57) ABSTRACT

A method for whitening teeth with a neat finishing, and a considerable durability can be provided at a low cost. Further, a method for easily making up nails can be provided. An apparatus of the present invention comprises a lower mold base for placing a male mold of a tooth form or a nail form to be attached with the seal, a sheet base for positioning a high polymer material sheet above the lower base, a holder portion for holding a female mold corresponding to the male mold, and a press mechanism for compressing the male mold, the high polymer material sheet placed on the sheet base, and the female mold with each other.

1 Claim, 8 Drawing Sheets

(FIG.1)
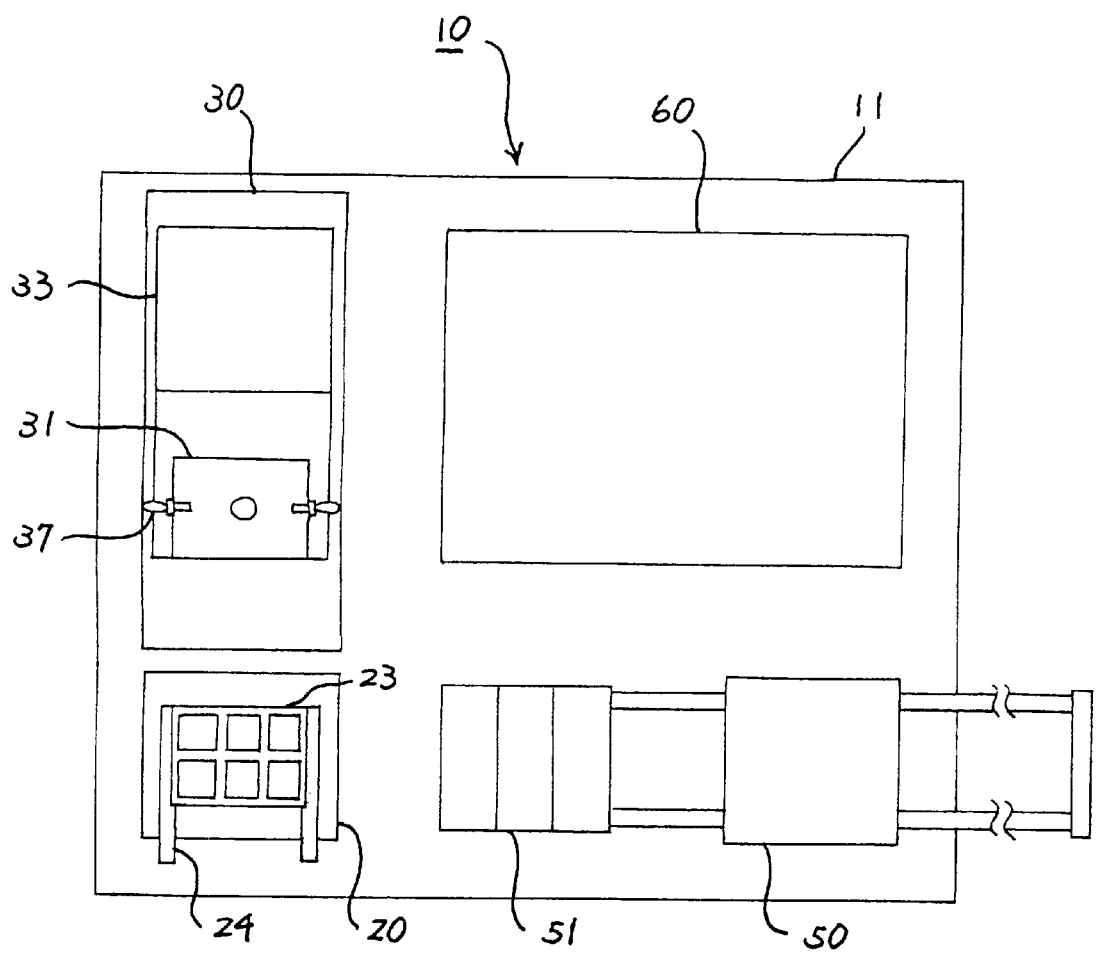

(FIG.2)
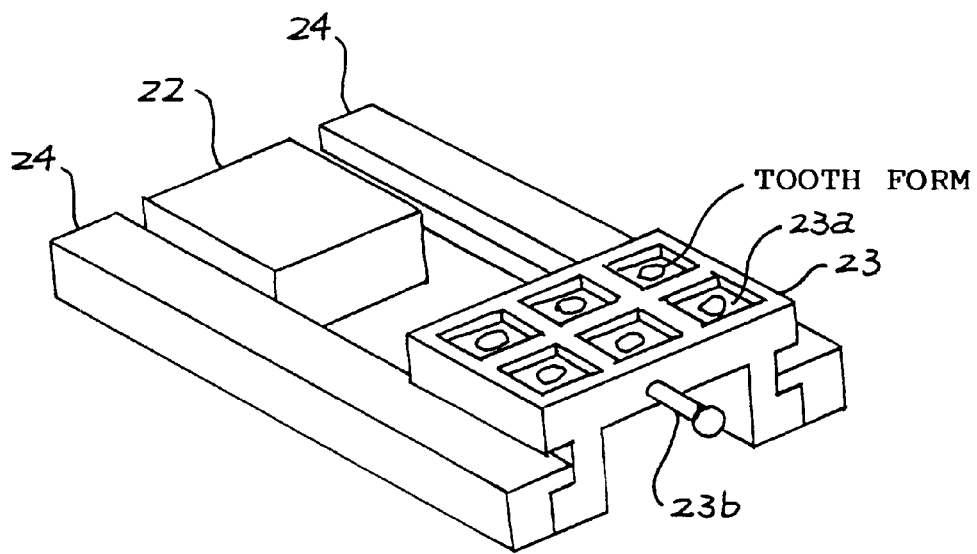
A
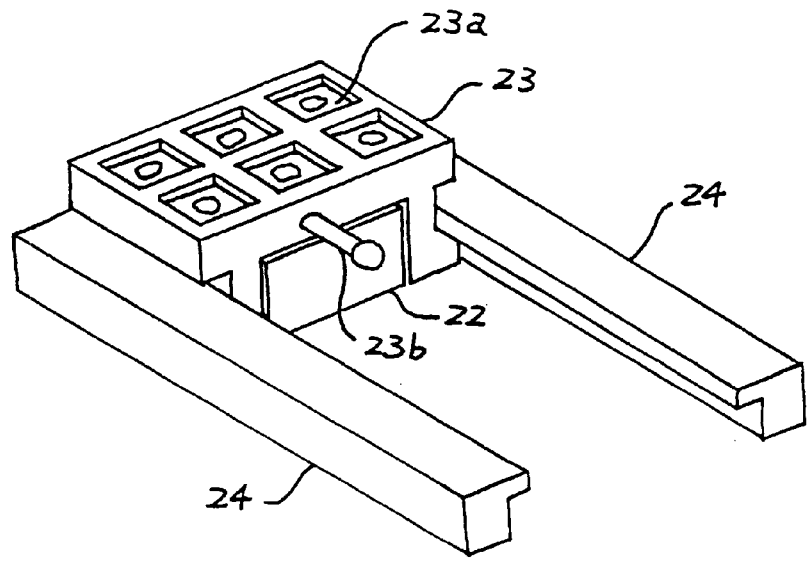
B (FIG.3)
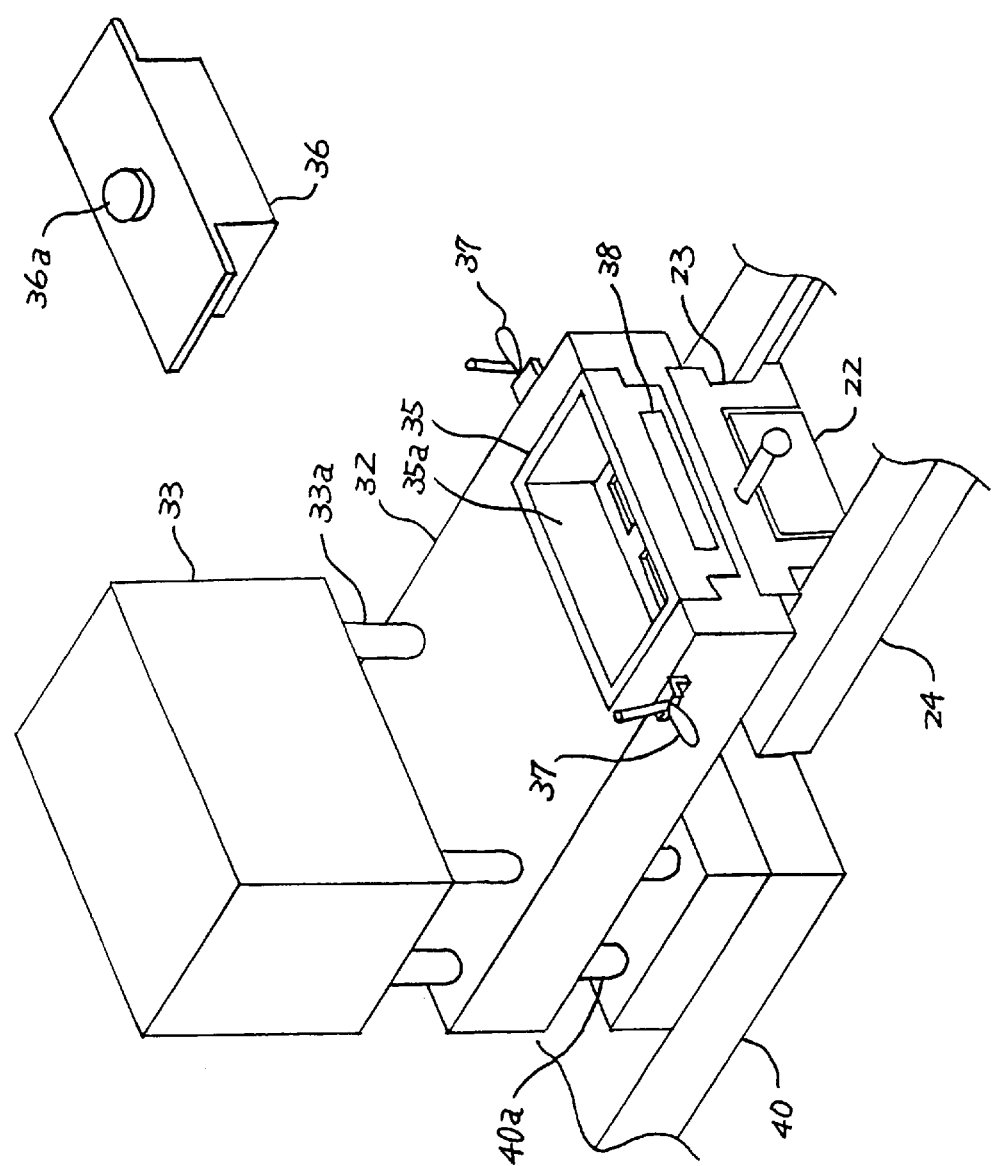

(FIG.4)
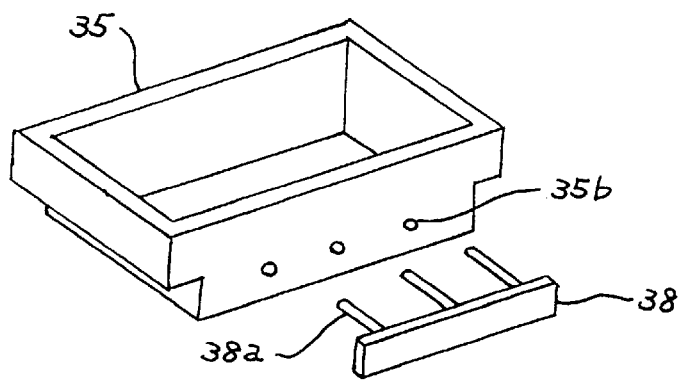
(FIG.5)
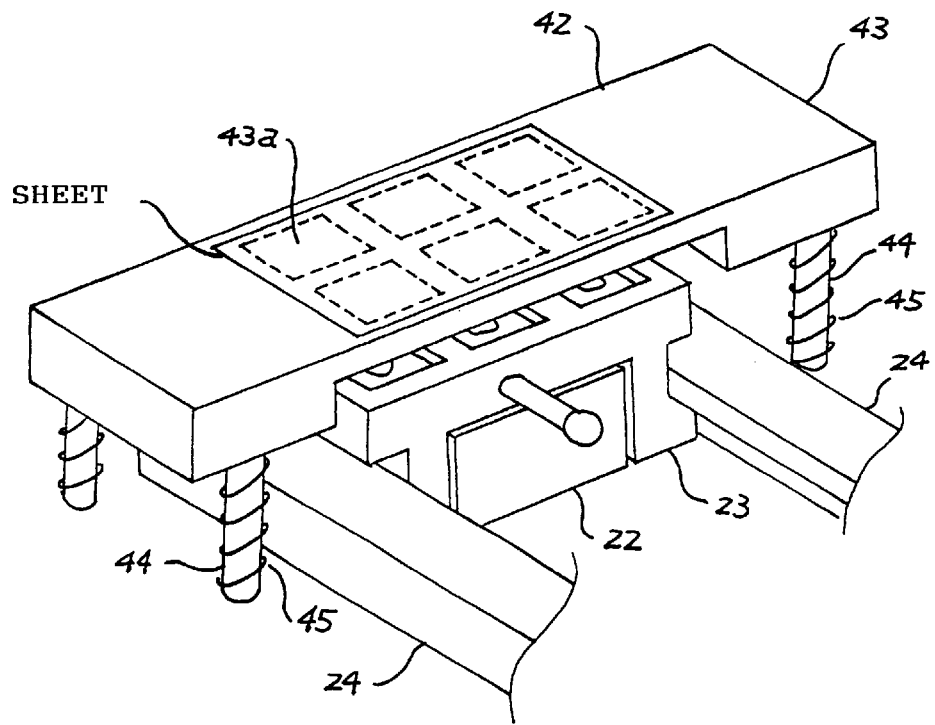

(FIG.6)
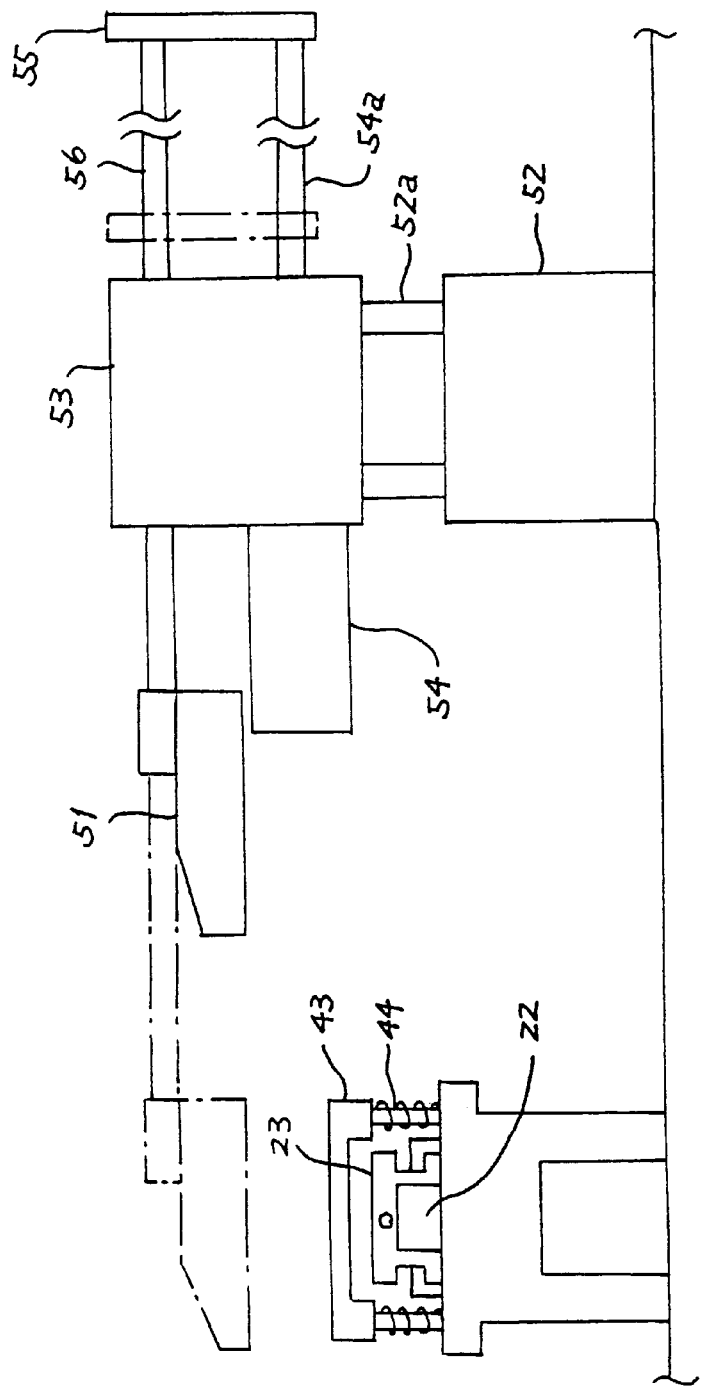

(FIG.7)
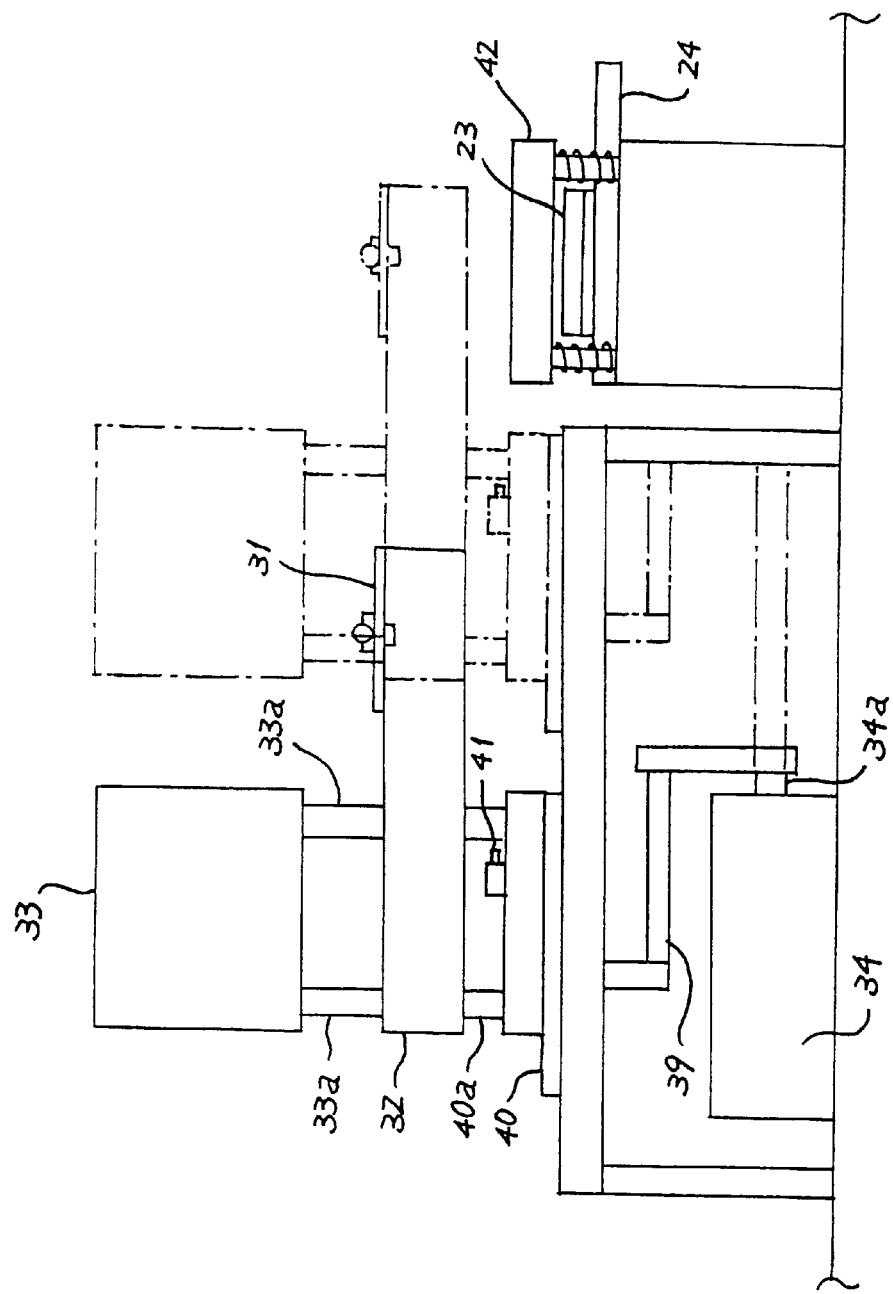

(FIG.8)
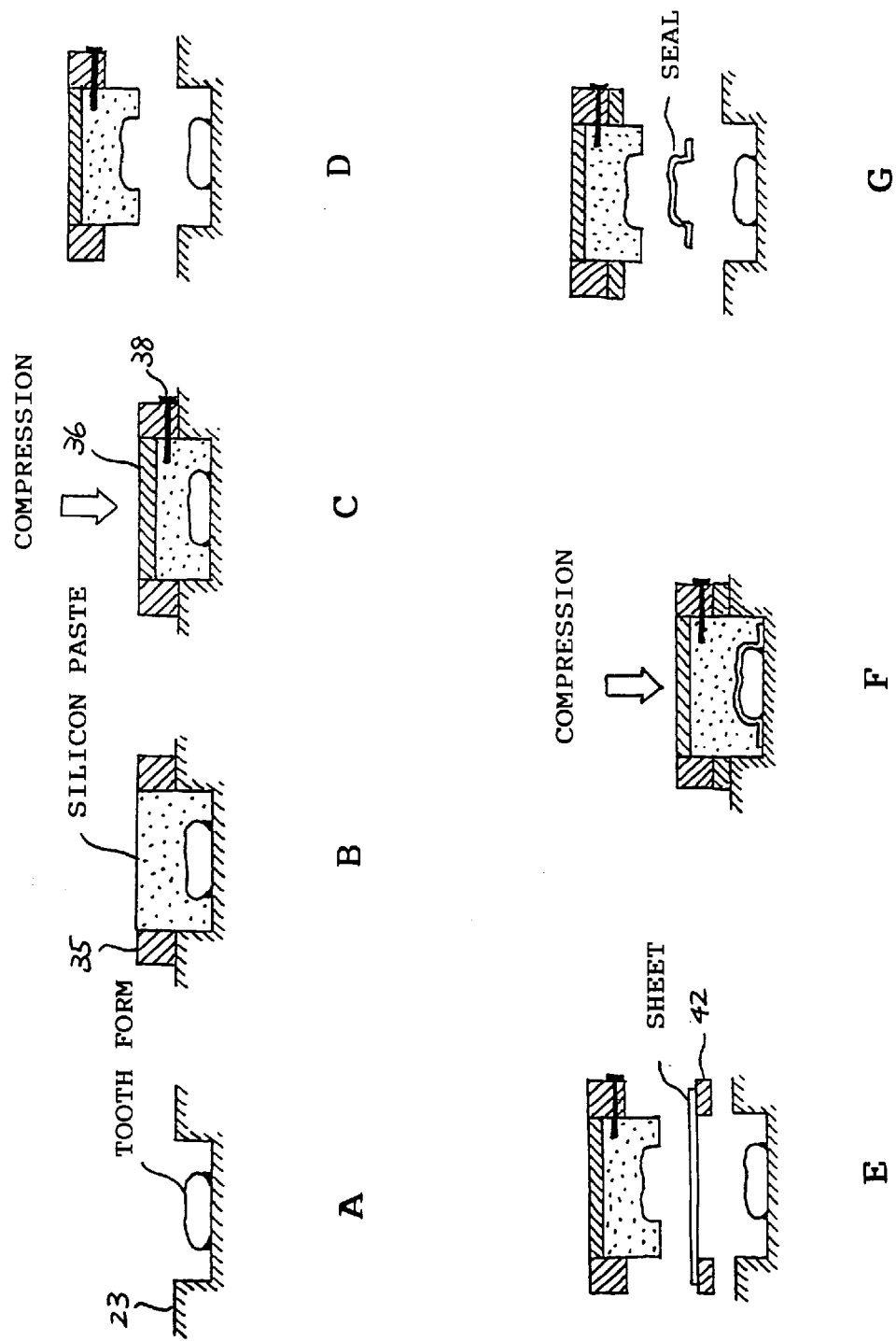

(FIG.9)
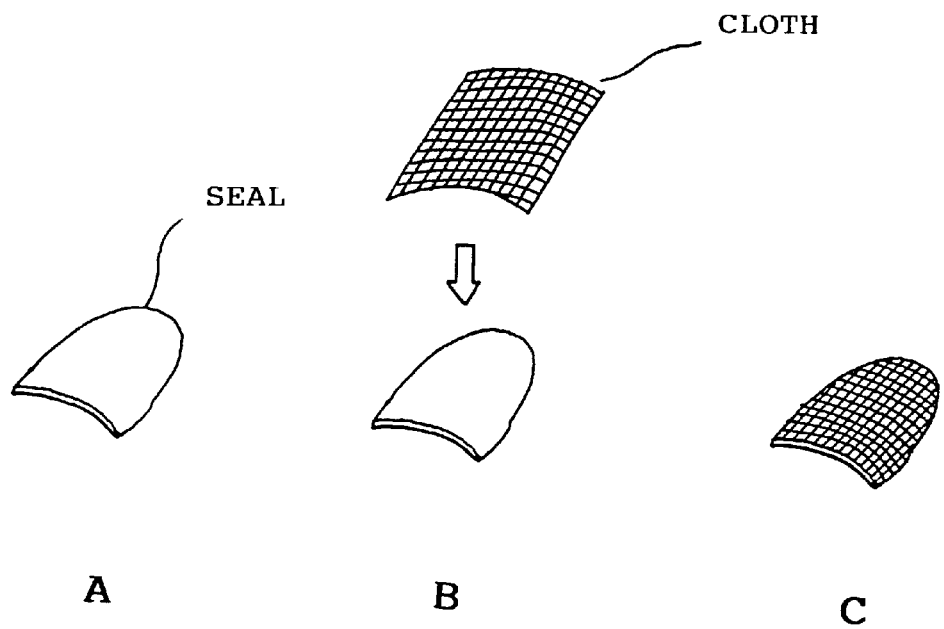
(FIG.10)
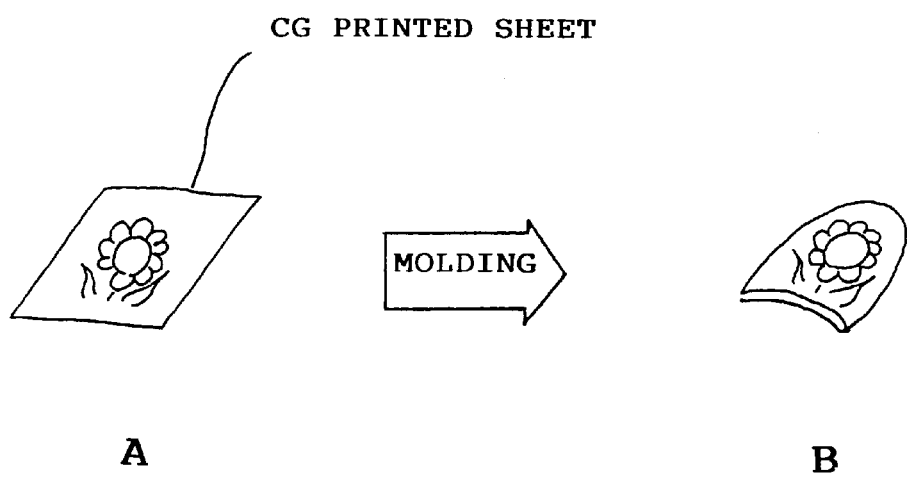

SEAL FOR HARD TISSUE, PRODUCING APPARATUS THEREFOR, AND METHOD FOR ATTACHING SEAL ON HARD TISSUE

BACKGROUND OF THE INVENTION

1. Field of the Invention

The present invention relates to a seal to be attached on hard tissues including a tooth or a nail (hereinafter referred to as a "seal") in particular, a seal producing apparatus, and a method for attaching the seal on the hard tissues.

2. Description of the Related Art

Demand for whiter teeth has been heightened recently. As odontological methods for whitening teeth, a method of bleaching teeth, a laminate veneer method, a manicure method, and the like are known. The method of bleaching teeth has setbacks such as uncertainty and necessity for applying the treatment many times. The laminate veneer method has setbacks such as a high cost and necessity of slightly abrading the teeth although neat finishing can be expected. Further, the manicure method has setbacks such as insufficient durability with the effect can be sustained only for about several hours. Accordingly, the conventional methods have both merits and demerits, but a satisfactory method has not been provided so far.

On the other hand, in the field of so-called nail art, nails are decorated by drawing a picture or a pattern directly thereon. However, there are tasks to be solved, such as necessity of time in applying the decoration, and trouble in removing the decoration. Besides, the risk of damaging nails is involved in the method. Therefore, a method for easily making up nails has been called for.

SUMMARY OF THE INVENTION

Accordingly, an object of the present invention is to provide a method for having whiter teeth with certainty, a neat finishing, and a considerable durability at a low cost. Further, another object of the present invention is to provide a method for easily making up nails.

A seal according to a first embodiment of the present invention is formed by compressing with each other a male mold of a tooth form or a nail form to be attached with the seal, a female mold corresponding to the male mold, and a high polymer material sheet provided therebetween.

A seal according to a second embodiment of the present invention comprises the seal according to the first embodiment, wherein the sheet is applied with an antibacterial agent or a substance having an antibacterial action.

A seal according to a third embodiment of the present invention comprises the seal according to the first or second embodiment, wherein the sheet is colored preliminarily to a desired white color.

A seal according to a fourth embodiment of the present invention comprises the seal according to the first or second embodiment, wherein a photograph of a tooth preliminarily prepared is printed on the sheet.

A seal according to a fifth embodiment of the present invention comprises the seal according to any of the first three embodiment, wherein a desired picture, photograph, or pattern is preliminarily printed on the sheet.

A seal according to a sixth embodiment of the present invention comprises the seal according to the first embodiment, wherein a desired cloth, paper, or leather is attached on the seal to be attached on a nail.

A seal according to a seventh embodiment of the present invention comprises the seal according to the first embodiment, wherein the seal to be attached on a nail is printed with computer graphics.

A seal producing apparatus according to an eight embodiment of the present invention comprises a lower mold base for placing a male mold of a tooth form or a nail form to be attached with the seal, a sheet base for positioning a high polymer material sheet above the lower base, a holder portion for holding a female mold corresponding to the male mold, and a press mechanism for compressing the male mold, the high polymer material sheet placed on the sheet base, and the female mold with each other.

A seal producing apparatus according to a ninth embodiment of the invention comprises the apparatus according to the eight embodiment, further comprising an upper heater mechanism for heating the sheet from above.

A seal producing apparatus according to a tenth embodiment of the invention comprises the apparatus according to the ninth embodiment, further comprising a lower heater mechanism for heating the sheet from below.

A method for attaching a seal on a tooth according to an eleventh embodiment of the invention comprises the steps of placing a high polymer material sheet between a male mold of a tooth form to be attached with the seal and a female mold corresponding to the male mold, applying an etching treatment on the front surface of the tooth to be attached with the seal, forming and cutting the sheet and adhering the cut seal on the tooth with a dental adhesive.

A method for attaching a seal on a tooth according to a twelfth embodiment of the invention comprises the method according to the eleventh embodiment, wherein the dental adhesive has a fluorine removability.

A method for attaching a seal on a tooth according to a thirteenth embodiment of the invention comprises the method according to the eleventh embodiment, wherein the dental adhesive contains an inorganic material such as apatite.

A method for attaching a seal on a nail according to a fourteenth embodiment of the invention comprises the step of adhering a seal on a nail with a tape applied with a pressure sensitive adhesive on both sides.

A method for attaching a seal on a nail according to a fifteenth embodiment of the invention comprises the method according to the fourteenth embodiment, wherein a pressure sensitive adhesive containing a medical component effective for growing a nail is applied at least one side of the tape.

A method for attaching a seal on a nail according to a sixteenth embodiment of the invention comprises the method according to the fifteenth embodiment, wherein the medical component effective for growing a nail is collagen.

BRIEF DESCRIPTION OF THE DRAWINGS

FIG. 1 is a schematic plan view showing a seal producing apparatus of the present invention.

FIGS. 2A and 2B are enlarged perspective views of a lower base of the seal producing apparatus. FIG. 2A shows the state where the lower base is detached from a lower heater. FIG. 2B shows the state where the lower base is close to the lower heater.

FIG. 3 is an enlarged perspective view showing a holder portion for forming male molds.

FIG. 4 is an enlarged perspective view showing a hook base and hook pins of the holder portion.

FIG. 5 is an enlarged perspective view showing the state where a sheet base is placed above the lower base.

FIG. 6 is a schematic side view showing the state of moving an upper heater mechanism.

FIG. 7 is a schematic side view showing the state of moving a press mechanism.

FIG. 8 is a diagram showing the production procedure of a seal.

FIG. 9 is a diagram showing the production process of a seal attached with a cloth on the surface, to be used in the field of nail art.

FIG. 10 is a diagram showing the production process of a seal applied with printing with CG, to be used in the field of nail art.

DESCRIPTION OF THE PREFERRED EMBODIMENT

Hereinafter an embodiment of the present invention on a seal to be attached on the front surface of a tooth will be explained in detail with reference to drawings. A seal producing apparatus according to one embodiment of the present invention referred to with numeral 10 in FIG. 1 as the entirety comprises a lower heater mechanism 20, a press mechanism 30, an upper heater mechanism 50, and a control mechanism 60 placed at a certain position on a base 11.

The lower heater mechanism 20 is a mechanism for heating a tooth form to serve as a male mold from below as described later in detail. As shown in FIGS. 6 and 7, the lower heater mechanism 20 has a table 21 and a lower heater 22 placed substantially on the center of the upper surface of the table 21.

A lower base 23 for placing the tooth form to serve as the male mold is placed on the upper surface of the table 21. As shown in FIGS. 2A and 2B well, the lower base 23 can slide between a first position away from the lower heater (see FIG. 2A) and a second position immediately above the lower heater 22 (see FIG. 2B) along a pair of guiding members 24 fixed on the upper surface of the table 21. The lower base 23 has concave portions 23a to place tooth forms (6 concave portions are shown in FIGS. 2A and 2B), and a lever 23b to serve as a handle portion in sliding the lower base 23.

The press mechanism 30 is a mechanism mainly for forming a seal by compressing a male mold, a female mold, and a sheet with each other as described later in detail. As shown in FIGS. 3 and 7, the press mechanism 30 has a holder portion 31 for placing the male mold, a press slider 32 to be attached with the holder portion 31, a press elevating cylinder 33 for elevating the press slider 32 (that is, the holder portion 31), and a press slide cylinder 34 for moving the press slider (that is, the holder portion 31) horizontally.

As shown in FIG. 3, the holder portion 31 having a holder 35 comprising a hollow portion 35a with the open upper part and lower part and a press holder 36 to be fitted to the hollow portion 35a of the holder 35, is mounted on the tip of the lower heater mechanism 20 side of the press slider 32. The planar size of the holder 35 is substantially the same as the planer size of the lower base 32. A knob 36a for holding the press holder 36 at the time of fitting or removing the press holder 36 to or from the hollow portion 35a of the holder 35 is provided in the press holder 36. A clamp 37 is mounted adjacent to the portion to be mounted with the holder 35 in the press slider 32 for pressing the press holder 36 at the time of fitting the press holder 36 to the hollow portion 35a of the holder 35.

FIG. 4 is an enlarged perspective view of the holder 35. As described later in detail, a male mold can be produced by injecting a silicon paste to the hollow portion 35a of the holder 35. Hook pins 38a interlocked by a hook base 38 are inserted to through holes 35b formed in the front surface of the holder 35 so as to prevent fall-off of the silicon paste after curing (that is, the male mold) from the holder 35.

As shown in FIG. 7, a piston rod 34a of a press slide cylinder 34 is interlocked to the press base 40 via a fixture 39 such that the press base 40 can be moved horizontally by extending or contracting the piston rod 34a. Further, as shown in FIG. 7, the piston rod 33a of the press elevating cylinder 33 is interlocked to the press slider 32 such that the press slider 32 can be moved vertically along a guiding member 40a fixed to the press base 40 by extending or contracting the piston rod 33a. The press elevating cylinder 33 and the press slide cylinder 34 can be driven by air supplied from an air compressor (not illustrated).

In FIG. 7, the state where the holder portion 31 is positioned above the lower base 23 by extending the piston rod 34a is shown with the chain line, and the state where the holder portion 31 is positioned away from the lower base 23 by contracting the piston rod 34a is shown with the solid line.

An air blowing opening 41 is provided to the press base 40 for jetting air for cooling a heated seal.

FIG. 5 shows a sheet base 42 for holding the sheet above the lower base 23. The sheet base 42 has a sheet base main body 43 having a rectangular planar shape and leg portions 44 provided at the four corners of the sheet base main body 43. To the sheet base main body 43, through holes 43a are provided at a position corresponding to the concave portions 34a of the lower base 23 when the sheet base 42 is positioned above the lower base 23. Springs 45 are mounted to each leg portion 44 such that the sheet base 42 can be lowered when force is applied to the sheet base 42 from above. The sheet is made from various polymer materials such as a vinyl chloride resin, acrylic and polypropylene, and polyethylene and preferably it is preliminarily colored to a white color suitable for the color of the tooth to be attached therewith.

The upper heater mechanism 50 is a mechanism for heating the sheet as later described in detail. As shown in FIG. 6, the upper heater mechanism 50 has a heater elevating cylinder 52 for elevating an upper heater 51 to be described later. A piston rod 52a of the heater elevating cylinder 52 is interlocked to a heater slide base 53. A heater slide cylinder 54 is attached to the heater slide base 53 for horizontally moving the upper heater 51, with a piston rod 54a of the heater slide cylinder 54 inserted through a through hole (not illustrated) provided in the heater slide base 53. A heater slide shaft 56 is attached to a mounting plate 55 fixed on the tip of the piston rod 54a of the heater slide cylinder 54. The heater slide shaft 56 is inserted through another through hole (not illustrated) provided in the heater slide base 53, with the upper heater 51 attached to the tip of the heater slide shaft 56.

According to the configuration of the upper heater mechanism 50, by extending or contracting the piston rod 52a of the heater elevating cylinder 52, the heater slide base 53 (that is, the upper heater 51) can be elevated or lowered, and by extending or contracting the piston rod 54a of the heater slide cylinder 54, the upper heater 51 can be moved horizontally. The heater elevating cylinder 52 and the heater slide cylinder 54 can be driven by air supplied from an air compressor (not illustrated).

In FIG. 6, the state where the upper heater 51 is positioned above the sheet base 41 by contracting the piston rod 54a of the heater slide cylinder 54 is shown with the chain line, and the state where the upper heater 51 is positioned away from the sheet base 41 is shown with the solid line by extending the piston rod 54*a*.

The control mechanism 60 is provided with a switch, a control circuit, a heater temperature indicating portion, a timer for setting the heating time, and the like for operating each part of the seal producing apparatus 10.

With reference to FIG. 8 schematically showing the production procedure of a seal, a method of producing a seal with the seal producing apparatus 10 will be explained. First, the lip side surface (front side) of the teeth is impressed. By forming a gypsum model by filling gypsum into the impression and dividing the obtained gypsum model for each one tooth, teeth forms to serve as the male molds can be produced.

Then, to the concave portions 23*a* of the lower base 23, the tooth forms are fixed with a heat-resistant fixing agent (see FIG. 8A). At the time, as shown in FIG. 2B, it is preferable to heat the tooth forms with the lower base 23 moved above the lower heater 22. The operation is for facilitating the sheet formation by heating the tooth forms, and it makes drastic temperature rise in heating the sheet with the upper heater 51 unnecessary.

Then, as shown with the chain line in FIG. 7, the holder portion 31 is positioned above the lower base 23 by operating the press slide cylinder 34 and the press elevating cylinder 33. A silicon paste is injected into the hollow portion 35*a* of the holder 35 (see FIG. 8B). Then, the silicon paste is compressed, utilizing the press holder 36 (see FIG. 8C). After curing the paste, the press elevating cylinder 33 is raised and the press slide cylinder 34 is withdrawn. The cured silicon paste becomes the male mold (see FIG. 8D).

Then, the sheet base 42 with the sheet thereon is placed above the lower base 23 (see FIG. 8E). At the time, as shown with the chain line of FIG. 6, it is preferable to heat the sheet with the upper heater 51 moved to a position above the sheet base 42. The operation is conducted since the sheet formation is facilitated by heating the sheet. When the sheet is heated to a predetermined temperature, the heater elevating cylinder 52 is raised and the heater slide cylinder 54 is withdrawn.

Then, by operating the press slide cylinder 34 and the press elevating cylinder 33, the holder portion 31 with the female mold placed thereon is positioned above the lower base 23 and the sheet base 42. By lowering the press elevating cylinder 33, the male mold, sheet, and the female mold are compressed from each other (see FIG. 8F). At the time, it is preferable to cool down the seal by jetting air from the air blowing opening 41 to the vicinity of the lower base 23, the sheet base 42, and the holder portion 31. The operation is conducted since the deformation of the seal can be prevented by cooling the heated seal, and the forming operation time can be reduced. After curing the sheet, the press elevating cylinder 33 is raised so as to obtain a seal fitting to the tooth form (see FIG. 8G).

The method of attaching a seal on a tooth will be explained. The seal accordingly obtained is divided for each one tooth. Then, the upper surface of the divided seals are applied with the sand blast treatment. Or a primer is applied on the rear side of the seals. Then, the surface of the teeth is applied with the etching treatment. The seals accordingly treated are adhered on the teeth surface with a dental adhesive. Finally, the trimming treatment is conducted for details.

The dental adhesive to be used for adhering seals preferably has a fluorine removability. By using an adhesive having a fluorine removability, the resistance to tooth decay can be facilitated. It is also preferable to use a dental adhesive containing an inorganic material such as apatite for adhering seals. By using a dental adhesive containing an inorganic material such as apatite for many times, the teeth themselves can be whiter.

An experiment was conducted to examine the durability of the seals attached with the above-mentioned method. In the experiment, alumina was used for the sand blast treatment, and maleic acid was used for the etching treatment. Phosphoric acid was not used for the etching treatment because by using phosphoric acid, the adherence of the seals to the teeth becomes so strong that the adhesive remains on the teeth even after the seals are peeled off. According to the result of the experiment with the above-mentioned condition, the seals remained on the teeth for more than one month.

The present invention is not limited to the above-mentioned embodiment but can be implemented with various modifications in the range specified in the following claims, and it is apparent that the modifications are also included in the range of the present invention.

For example, in the above-mentioned embodiment, seals made from a polymer material are used. However, if the seals are attached on the teeth for a long time, there is a risk in that germs may generate by the plaque adhered on the seals. Therefore, in order to prevent the risk, it is preferable to use a seal with an antibacterial agent applied thereon. Examples of the antibacterial agent include a silver antibacterial agent and a ceramic antibacterial agent. Further, a substance having an antibacterial function (such as chitin chitosan) can be used instead of an antibacterial agent. By using a seal with an antibacterial agent applied thereon, the effect of preventing tooth decay and *pyorrhea alveolaris* in the vicinity of the seal can be expected.

A test conducted for proving the effect of the seal with a silver antibacterial agent applied thereon will be explained. As a test piece, a ball of an immediate polymerizing type resin (Olsofast) with a 12.3 mm diameter with a silver antibacterial agent contained therein was prepared. As the silver antibacterial agent, Bactekiller commercially available from Kanebo Kasei Corp. was used. As a test piece to be compared, a ball of the immediate polymerizing type resin not containing the silver antibacterial agent was used.

In testing, the above-mentioned test pieces were fertilized in test tubes containing 10 ml of a liquid medium (BHI) containing 1% by weight of sucrose. Then, the test tubes were preliminarily maintained at 37° C. for 7 days. 1 ase of a culture solution of test strain was inoculated to the test pieces, followed by 24 hours culture at 37° C. The bacteria used were *Streptococcus salivarius* ATCC 9222, *Streptococcus mitis* ATCC 9811, *Streptococcus mutans* LM7, *Streptococcus mutans* OMZ 175, *Streptococcus mutans* JC2, and *Streptococcus mutans* GS5.

After 24 hours from the inoculation, the culture solutions inoculated with *Streptococcus salivarius* ATCC 9222, *Streptococcus mitis* ATCC 9811, and *Streptococcus mutans* GS5 became unclear so as to confirm the antibacterial action.

As a result, after 6 hours from the inoculation, the culture solution inoculated with *Streptococcus mutans* LM7, *Streptococcus mutans* OMZ 175 and *Streptococcus mutans* JC2 also became turbid so as to confirm the antibacterial action.

Although the explanation has been given for a seal for providing a white tooth, a seal of the present invention can be used also in the field of so-called tooth art by attaching a seal printed with a picture, a photograph, or a pattern, on a tooth. In this case, a transparent synthetic resin material (such as a vinyl sheet) can be coated on the surface of the printed picture, and the like so as to prevent a hazardous component in the ink spread in the mouth. Further, by printing a picture, a photograph, and the like on a sheet with computer processing, a seal can be produced at a low cost. It is also possible to realize a whiteness similar to genuine teeth by taking a photograph of beautiful teeth and printing the photograph on seals.

Furthermore, in the field of so-called nail art by attaching a seal on a nail, a seal of the present invention can be used. FIG. 9 shows a production process of a seal with a cloth attached on the surface. In this embodiment, a seal corresponding to the form of the nail to be attached is produced as mentioned above (see FIG. 9A). A desired cloth is attached on the seal with an adhesive (see FIG. 9B). Thereafter by trimming the cloth so as to fit to the nail shape (see FIG. 9C), a seal for the nail art application can be produced. In this case, paper or leather can be attached instead of a cloth.

FIG. 10 shows an example of the application of a seal in the field of nail art as FIG. 9. It shows the production process of a seal applied with printing by computer graphics (CG). In this embodiment, before forming, a sheet is preliminarily applied with printing by CG (see FIG. 10A). As the software of CS to be used, either of one specially prepared for a seal of the present invention or one commercially available can be used. The sheet (CG printed sheet) is molded so as to correspond with the shape of a nail to be attached as mentioned above. Thereafter, the seal is trimmed so as to fit to the nail form (see FIG. 10B).

The seals explained with reference to FIGS. 9 and 10 can be attached on a nail with a tape applied with a pressure sensitive adhesive applied on both sides (hereinafter referred to as "both side tape"). It is preferable that the pressure sensitive adhesive contains a medical component effective for growing a nail (such as collagen) is applied at least one side of the tape. Further, the seal of the present invention may be manufactured by methods other than the methods described herein before. Thus it may be manufactured by a method utilizing vacuum, which comprises steps of locating the sheet above the male mold of a nail or tooth heating the sheet; approaching the softend sheet to the molded and drawing the sheet from below by utilizing vacuum. Further for forming the sheet by using female and male molds, the female mold may be substituted by a sponge.

According to the present invention, it is possible to have white teeth with a considerable durability and a neat finishing at a comparatively low cost. By using a seal applied with an antibacterial agent, generation of germs in the mouth can be prevented, as well as tooth decay and *pyorrhea alveolaris* can be prevented in the vicinity of the seal. By using an adhesive having a fluorine removability, the resistance to tooth decay can be facilitated. By using a dental adhesive containing an inorganic material such as apatite for many times, the teeth themselves become whiter. A whiteness similar to genuine teeth can be realized by taking a photograph of beautiful teeth and printing the photograph on seals. Moreover, it can be used for the tooth art. Furthermore, it can be applied for the nail art. Particularly in the field of the nail art, by attaching a desired cloth, paper, or leather or applying printing with CG on a seal, a unique make-up can be enjoyed easily at a low cost.

What is claimed is:

1. A seal for hard tissues such as tooth, formed by compressing a vinyl chloride sheet between a male mold of a tooth form to be attached with the seal and a female mold corresponding to the male mold, wherein a photograph of a tooth preliminarily prepared is printed on the sheet.

* * * * *